United States Patent
Hamdan et al.

(10) Patent No.: US 7,821,260 B2
(45) Date of Patent: Oct. 26, 2010

(54) NMR ECHO TRAIN COMPRESSION USING ONLY NMR SIGNAL MATRIX MULTIPLICATION TO PROVIDE A LOWER TRANSMISSION BIT PARAMETRIC REPRESENTATION FROM WHICH ESTIMATE VALUES OF EARTH FORMATION PROPERTIES ARE OBTAINED

(75) Inventors: Mouin Hamdan, Niedersachsen (DE); Holger F. Thern, Hannover (DE); Thomas Kruspe, Wietzendorf (DE); Peter Rottengatter, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 169 days.

(21) Appl. No.: 12/029,905

(22) Filed: Feb. 12, 2008

(65) Prior Publication Data
US 2008/0183390 A1  Jul. 31, 2008

Related U.S. Application Data

(63) Continuation-in-part of application No. 11/845,983, filed on Aug. 28, 2007, now abandoned, which is a continuation-in-part of application No. 11/084,322, filed on Mar. 18, 2005, now Pat. No. 7,495,436.

(60) Provisional application No. 60/841,694, filed on Sep. 1, 2006.

(51) Int. Cl.
*G01V 3/00* (2006.01)

(52) U.S. Cl. .................... 324/303; 324/314

(58) Field of Classification Search ............... 324/303, 324/306, 309, 314, 318, 321; 702/11, 6; 600/410, 420
See application file for complete search history.

(56) References Cited

U.S. PATENT DOCUMENTS 4,973,111 A  11/1990  Haacke et al.
5,023,551 A  6/1991  Kleinberg et al.
(Continued)

FOREIGN PATENT DOCUMENTS

EP  0981062 A2  2/2000
(Continued)

OTHER PUBLICATIONS

M. N. Miller et al.; Spin Echo Magnetic Resonance Logging: Porosity and Free Fluid Index Determination, SPE 20561, 65th Annual Technical Conference and Exhibition of the Society of Petroleum Engineers, New Orleans, Sep. 23-28, 1990, pp. 321-334.

*Primary Examiner*—Brij B. Shrivastav
*Assistant Examiner*—Tiffany A Fetzner
(74) *Attorney, Agent, or Firm*—Mossman Kumar & Tyler PC

(57) ABSTRACT

NMR spin echo signals are acquired downhole. An independent component analysis is used to determine parameters of a parametric model of the $T_2$ distribution whose output matches the measurements. The model parameters are telemetered to the surface where the properties of the formation are reconstructed. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims. 37 CFR 1.72(b).

18 Claims, 5 Drawing Sheets

U.S. PATENT DOCUMENTS

| | | | |
|---|---|---|---|
| 5,055,787 A | 10/1991 | Kleinberg et al. | |
| 5,121,337 A | 6/1992 | Brown | |
| 5,280,243 A | 1/1994 | Miller | |
| 5,291,137 A * | 3/1994 | Freedman | 324/303 |
| 5,363,041 A | 11/1994 | Sezginer | |
| 5,381,092 A * | 1/1995 | Freedman | 324/303 |
| 5,486,762 A * | 1/1996 | Freedman et al. | 324/303 |
| 5,517,115 A | 5/1996 | Prammer | |
| 5,557,200 A | 9/1996 | Coates | |
| 5,557,201 A | 9/1996 | Kleinberg et al. | |
| 5,696,448 A | 12/1997 | Coates et al. | |
| 5,698,979 A | 12/1997 | Taicher et al. | |
| 5,764,058 A | 6/1998 | Itskovich et al. | |
| 5,936,405 A | 8/1999 | Prammer et al. | |
| 6,040,696 A | 3/2000 | Ramakrishnan et al. | |
| 6,215,304 B1 | 4/2001 | Slade | |
| 6,242,912 B1 | 6/2001 | Prammer et al. | |
| 6,400,148 B1 | 6/2002 | Meyer et al. | |
| 6,420,869 B1 | 7/2002 | DiFoggio | |
| 6,512,371 B2 | 1/2003 | Prammer | |
| 6,541,969 B2 | 4/2003 | Sigal et al. | |
| 6,646,437 B1 | 11/2003 | Chitale et al. | |
| 6,796,497 B2 | 9/2004 | Benkert et al. | |
| 6,859,032 B2 * | 2/2005 | Heaton et al. | 324/303 |
| 6,859,033 B2 * | 2/2005 | Speier | 324/303 |
| 6,868,736 B2 | 3/2005 | Sawatari et al. | |
| 6,937,014 B2 * | 8/2005 | Sun et al. | 324/303 |
| 7,034,528 B2 | 4/2006 | Minh et al. | |
| 2002/0153887 A1 | 10/2002 | Taicher | |
| 2002/0167314 A1 | 11/2002 | Prammer | |
| 2003/0128032 A1 * | 7/2003 | Heaton et al. | 324/303 |
| 2003/0231017 A1 | 12/2003 | Kiesl et al. | |
| 2004/0041562 A1 | 3/2004 | Speier | |
| 2004/0169511 A1 * | 9/2004 | Minh et al. | 324/303 |
| 2004/0189296 A1 * | 9/2004 | Sun et al. | 324/306 |
| 2005/0206378 A1 | 9/2005 | Hamdan et al. | |
| 2005/0216196 A1 * | 9/2005 | Akkurt et al. | 702/6 |
| 2008/0036457 A1 | 2/2008 | Thern et al. | 324/303 |
| 2008/0183390 A1 * | 7/2008 | Hamdan et al. | 702/11 |
| 2009/0174402 A1 * | 7/2009 | Rottengatter et al. | 324/303 |
| 2009/0292473 A1 * | 11/2009 | Kruspe et al. | 702/8 |

FOREIGN PATENT DOCUMENTS

EP          1003053 A2     5/2000

* cited by examiner

NMR ECHO TRAIN COMPRESSION USING ONLY NMR SIGNAL MATRIX MULTIPLICATION TO PROVIDE A LOWER TRANSMISSION BIT PARAMETRIC REPRESENTATION FROM WHICH ESTIMATE VALUES OF EARTH FORMATION PROPERTIES ARE OBTAINED

CROSS-REFERENCES TO RELATED APPLICATIONS

This application is a continuation-in-part of U.S. patent application Ser. No. 11/845,983 filed on Aug. 28, 2007 now abandoned, which application claimed priority from U.S. Provisional Patent Application Ser. No. 60/841,694 filed on Sep. 1, 2006 and is also a continuation in part of U.S. patent application Ser. No. 11/084,322 of Hamdan et al filed on Mar. 18, 2005 now U.S. Pat. No. 7,495,436.

BACKGROUND OF THE DISCLOSURE

1. Field of the Disclosure

The present disclosure relates generally to determining geological properties of subsurface formations using Nuclear Magnetic Resonance ("NMR") methods for logging wellbores, particularly for representing NMR echo trains by a limited number of functional parameters, enabling efficient transmission of echo train from a downhole location.

2. Description of the Related Art

NMR methods are among the most useful non-destructive techniques of material analysis. When hydrogen nuclei are placed in an applied static magnetic field, a small majority of spins are aligned with the applied field in the lower energy state, since the lower energy state in more stable than the higher energy state. The individual spins precess about the applied static magnetic field at a resonance frequency also termed as Larmor frequency. This frequency is characteristic to a particular nucleus and proportional to the applied static magnetic field. An alternating magnetic field at the resonance frequency in the Radio Frequency (RF) range, applied by a transmitting antenna to a subject or specimen in the static magnetic field flips nuclear spins from the lower energy state to the higher energy state. When the alternating field is turned off, the nuclei return to the equilibrium state with emission of energy at the same frequency as that of the stimulating alternating magnetic field. This RF energy generates an oscillating voltage in a receiver antenna whose amplitude and rate of decay depend on the physicochemical properties of the material being examined. The applied RF field is designed to perturb the thermal equilibrium of the magnetized nuclear spins, and the time dependence of the emitted energy is determine by the manner in which this system of spins return to equilibrium magnetization. The return is characterized by two parameters: $T_1$, the longitudinal or spin-lattice relaxation time; and $T_2$, the transverse or spin-spin relaxation time.

Measurements of NMR parameters of fluid filling the pore spaces of the earth formations such as relaxation times of the hydrogen spins, diffusion coefficient and/or the hydrogen density is the bases for NMR well logging. NMR well logging instruments can be used for determining properties of earth formations including the fractional volume of pore space and the fractional volume of mobile fluid filling the pore spaces of the earth formations.

One basic problem encountered in NMR logging or MRI imaging is the vast amount of data that has to be analyzed. In well logging with wireline instruments, the downhole processing capabilities are limited as is the ability to transmit data to an uphole location for further analysis since all the data are typically sent up a wireline cable with limited bandwidth. In the so-called Measurement-while-drilling methods, the problem is exacerbated due to the harsh environment in which any downhole processor must operate and to the extremely limited telemetry capability: data are typically transmitted at a rate of no more than twenty bits per second.

A second problem encountered in NMR logging and MRI imaging is that of analysis of the data. As will be discussed below, the problem of data compression and of data analysis are closely inter-related.

Methods of using NMR measurements for determining the fractional volume of pore space and the fractional volume of mobile fluid are described, for example, in *Spin Echo Magnetic Resonance Logging: Porosity and Free Fluid Index Determination*, M. N. Miller et al, Society of Petroleum Engineers paper no. 20561, Richardson, Tex., 1990. In porous media there is a significant difference in $T_1$ and $T_2$ relaxation time spectrum of fluids mixture filling the pore space. Thus, for example, light hydrocarbons and gas may have $T_1$ relaxation time of about several seconds, while $T_2$ may be a few milliseconds. This phenomenon is due to diffusion effect in internal and external static magnetic field gradients. Internal magnetic field gradients are due to magnetic susceptibility difference between rock formation matrix and pore filling fluid.

Since oil is found in porous rock formation, the relationship between porous rocks and the fluids filling their pore spaces are extremely complicated and difficult to model. Nuclear magnetic resonance is sensitive to main petrophysical parameters, but has no capabilities to establish these complex relationships. Oil and water are generally found together in reservoir rocks. Since most reservoir rocks are hydrophilic, droplets of oil sit in the center of pores and are unaffected by the pore surface. The water-oil interface normally does not affect relaxation, therefore, the relaxation rate of oil is primarily proportional to its viscosity. However, such oil by itself is a very complex mixture of hydrocarbons that may be viewed as a broad spectrum of relaxation times. In a simplest case of pure fluid in a single pore, there are two diffusion regimes that govern the relaxation rate. Rocks normally have a very broad distribution of pore sizes and fluid properties. Thus it is not surprising that magnetization decays of fluid in rock formations are non-exponential. The most commonly used method of analyzing relaxation data is to calculate a spectrum of relaxation times. The Carr-Purcell-Meiboom-Gill (CPMG) pulse sequence is used to determine the transverse magnetization decay. The non-exponential magnetization decays are fit to the multi-exponential form:

$$M(t) = \sum_{i=1}^{L} m(T_{2i}) e^{-t/T_{2i}} \qquad (1)$$

where M(t) represents the spin echo amplitudes, equally spaced in time, and the $T_{2i}$ are predetermined time constants, equally spaced on a logarithm scale, typically between 0.3 ms and 3000 ms. The set of m are found using a regularized nonlinear least squares technique. The function $m(T_{2i})$, conventionally called a $T_2$ distribution, usually maps linearly to a volumetrically weighted distribution of pore sizes.

The calibration of this mapping is addressed in several publications. Prior art solutions seek a solution to the problem of mathematical modeling the received echo signals by the use of several techniques, including the use of non-linear regression analysis of the measurement signal; non-linear least square fit routines, as disclosed in U.S. Pat. No. 5,023,551 to Kleinberg et al, and others. Other prior art techniques include a variety of signal modeling techniques, such as polynomial rooting, singular value decomposition (SVD) and miscellaneous refinements thereof, to obtain a better approximation of the received signal. A problem with prior art signal compressions is that some information is lost.

Other methods of compression of NMR data are discussed, for example in U.S. Pat. No. 4,973,111 to Haacke and U.S. Pat. No. 5,363,041 to Sezginer. Inversion methods discussed in the two references generally are computationally intensive and still end up with a large number of parameters that have to be transmitted uphole. In particular, no simple methods have been proposed to take advantage of prior knowledge about the structure of the investigated material and the signal-to-noise (SNR) ratio of the received echo signal. Also, no efficient solutions have been proposed to combine advanced mathematical models with simple signal processing algorithms to increase the accuracy and numerical stability of the parameter estimates. Finally, existing solutions require the use of significant computational power which makes the practical use of those methods inefficient, and frequently impossible to implement in real-time applications.

SUMMARY OF THE DISCLOSURE

One embodiment of the disclosure is a method of determining a property of an earth formation. The method includes conveying a nuclear magnetic resonance (NMR) sensing apparatus into a borehole, using the NMR sensing apparatus for obtaining a signal indicative of the property of the earth formation, using a predetermined matrix to estimate from the signal a parametric representation of the relaxation of nuclear spins in terms of at least one basis function, telemetering the parametric representation to a surface location and, at the surface location, using the telemetered parametric representation to estimate the property of the earth formation. The signal may be a spin echo signal and representation of relaxation of nuclear spins may include a transverse relaxation time ($T_2$) distribution. The at least one basis function may be a Gaussian function, and parametric representation may include a mean, a standard deviation, and an amplitude of the Gaussian function. Defining the predetermined matrix may be done by for performing regression analysis on synthetic NMR signals and/or NMR signals measured on samples having known properties. The dependent variable in the independent component analysis may be a spin echo signal. The determined property may be bound volume irreducible, effective porosity, bound water, clay-bound water, total porosity, a permeability, and/or a pore size distribution. The regression analysis may be a partial least-squares, a principal component regression, independent component regression, an inverse least-squares, a ridge regression, a Neural Network, a neural net partial least-squares regression, and/or a locally weighted regression. The NMR sensing apparatus may be conveyed into the borehole on a bottomhole assembly using a drilling tubular.

Another embodiment of the disclosure is an apparatus for determining a property of an earth formation. The apparatus includes a nuclear magnetic resonance (NMR) sensing apparatus configured to be conveyed into a borehole and obtain a signal indicative of the property of the earth formation. The apparatus also includes a downhole processor configured to use a predetermined matrix to estimate from the signal a parametric representation of the relaxation of nuclear spins in terms of at least one basis function, telemeter the parametric representation to a surface location, and a surface processor configured to use with the telemetered parametric representation estimate the property of the formation. The signal that the NMR sensing apparatus is configured to produce may include a spin echo signal, and representation of relaxation of nuclear spins further may include a transverse relaxation time $T_2$ distribution. The at least one basis function that the downhole processor is configured to use may include a Gaussian function, and the parametric representation estimated by the downhole processor may include a mean, a standard deviation, and an amplitude of the Gaussian function. The predetermined matrix may be defined by a processor configured to perform regression analysis on synthetic NMR signals and/or NMR signals measured on samples having known properties. The dependent variable in the regression analysis may be a spin echo signal. The property the surface processor is configured to determine may be bound volume irreducible, effective porosity, bound water, clay-bound water, total porosity, a permeability, and/or a pore size distribution. The regression analysis may be a partial least-squares, a principal component regression, an independent component regression, an inverse least-squares, a ridge regression, a Neural Network, a neural net partial least-squares regression, and/or a locally weighted regression. The apparatus may include a drilling tubular configured to convey a bottomhole assembly including the NMR sensing device into the borehole.

Another embodiment of the disclosure is at least one computer-readable medium for use with an apparatus for determining a property of an earth formation. The apparatus includes a nuclear magnetic resonance (NMR) sensing apparatus configured to be conveyed into the borehole and produce a signal indicative of the property of the earth formation. The at least one computer readable medium includes instructions which enable a downhole processor to use a predetermined matrix to estimate from the signal a parametric representation of relaxation of nuclear spins in terms of at least one basis function and telemeter the parametric representation to a surface location. Also included are instructions which enable a surface processor to use the telemetered parametric representation to estimate the property of the earth formation. The medium may be a ROM, an EPROM, an EEPROM, a flash memory, and/or an optical disk.

BRIEF DESCRIPTION OF THE DRAWINGS

The present disclosure is best understood with reference to the accompanying figures in which like numerals refer to like elements and in which.

DETAILED DESCRIPTION OF THE DISCLOSURE

Figure 1:
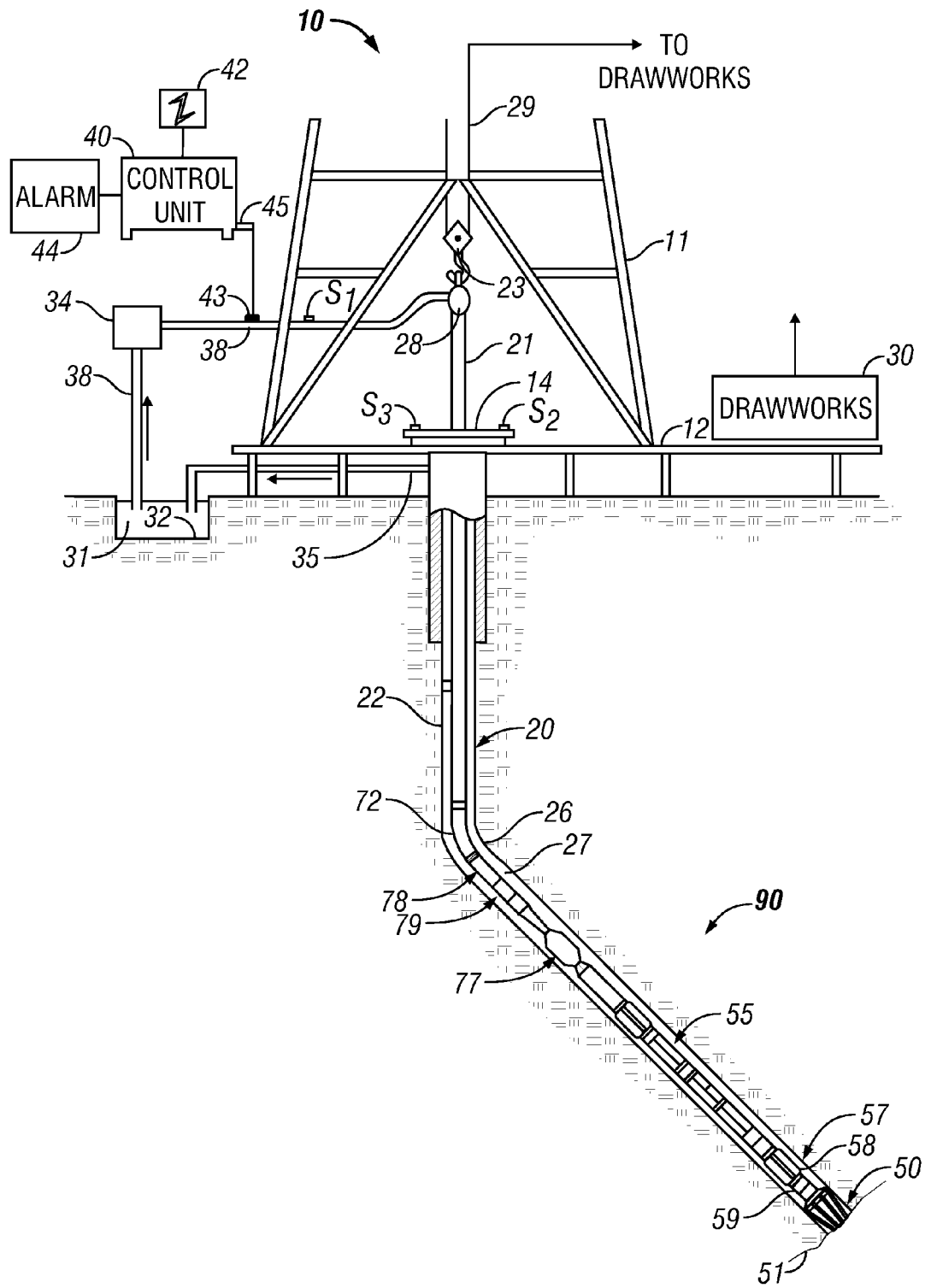
FIG. 1 (prior art) shows a measurement-while-drilling tool suitable for use with the present disclosure.

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein. For the purposes of this disclosure, it is necessary to know the axial velocity (rate of penetration or ROP) of the bottomhole assembly. Depth information and ROP may be communicated downhole from a surface location. Alternatively, the method disclosed in U.S. Pat. No. 6,769,497 to Dubinsky et al. having the same assignee as the present application and the contents of which are incorporated herein by reference may be used. The method of Dubinsky uses axial accelerometers to determine the ROP. During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralize for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

A suitable device for use of the present disclosure is disclosed in U.S. Pat. No. 6,215,304 to Slade, the contents of which are fully incorporated herein by reference. It should be noted that the device taught by Slade is for exemplary purposes only, and the method of the present disclosure may be used with many other NMR logging devices, and may be used for wireline as well as MWD applications. Examples of such devices are given in U.S. Pat. No. 5,557,201 to Kleinberg, U.S. Pat. No. 5,280,243 to Miller, U.S. Pat. No. 5,055,787 to Kleinberg, and U.S. Pat. No. 5,698,979 to Taicher.

Figure 2:
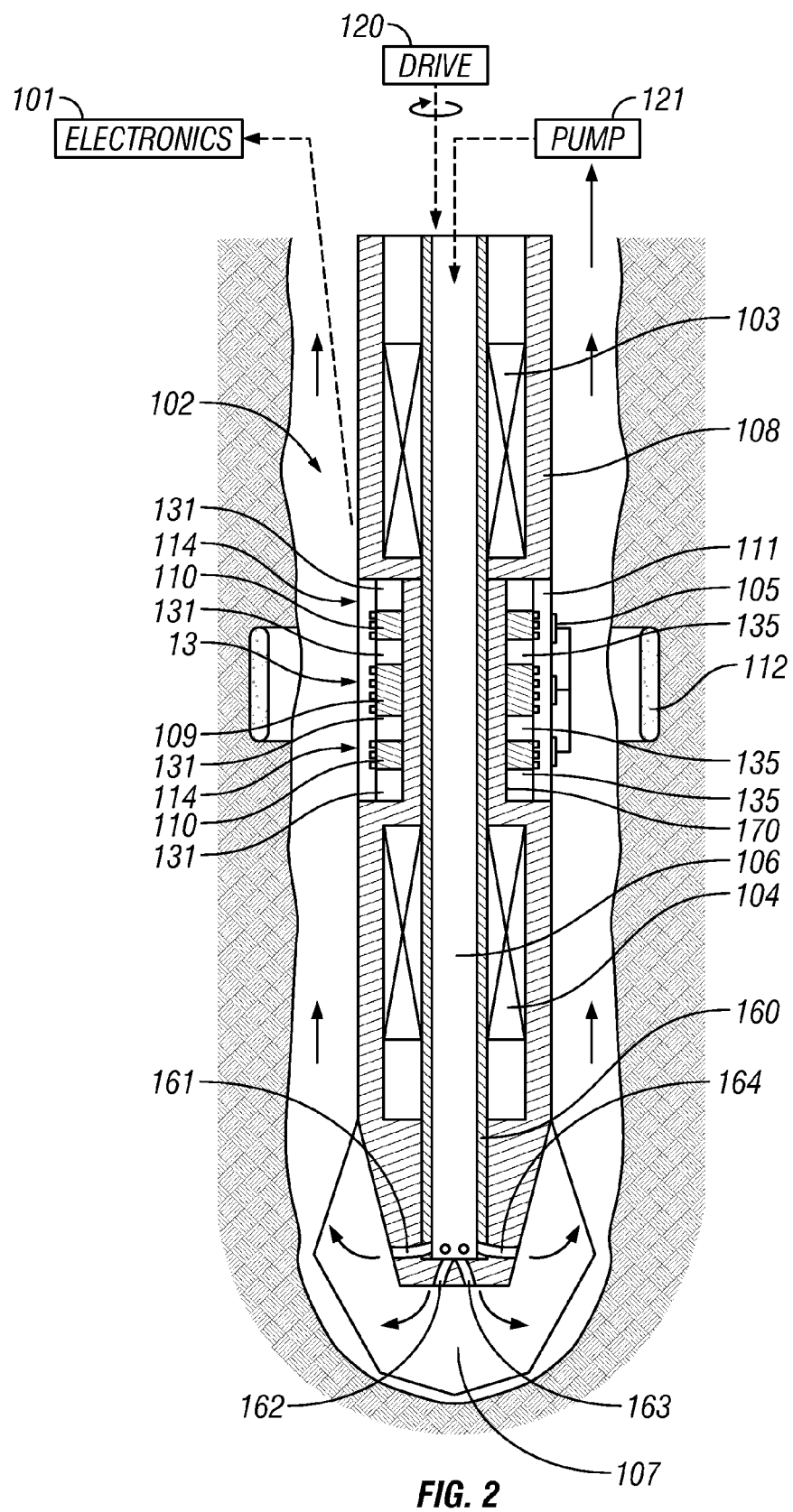
FIG. 2 (prior art) shows a sensor section of a measurement-while-drilling device suitable for use with the present disclosure.

Referring now to FIG. 2, the tool has a drill bit 107 at one end, a sensor section 102 behind the drill head, and electronics 101. The sensor section 102 comprises a magnetic field generating assembly for generating a $B_0$ magnetic field (which is substantially time invariant over the duration of a measurement), and an RF system for transmitting and receiving RF magnetic pulses and echoes. The magnetic field generating assembly comprises a pair of axially spaced main magnets 103, 104 having opposed pole orientations (i.e. with like magnetic poles facing each other), and three ferrite members 109, 110 axially arranged between the magnets 103, 104. The ferrite members are made of "soft" ferrite which can be distinguished over "hard" ferrite by the shape of the BH curve which affects both intrinsic coercivity ($H_j$ the intersection with the H axis) and initial permeability ($\mu_i$, the gradient of the BH curve in the unmagnetized case). Soft ferrite $\mu_i$ values typically range from 10 to 10000 whereas hard ferrite has $\mu_i$, of about 1. Therefore the soft ferrite has large initial permeability (typically greater than 10, preferably greater than 1000). The RF system comprises a set of RF transmit antenna and RF receive antenna coil windings 105 arranged as a central "field forming" solenoid group 113 and a pair of outer "coupling control" solenoid groups 114.

The tool has a mud pipe 160 with a clear central bore 106 and a number of exit apertures 161-164 to carry drilling mud to the bit 107, and the main body of the tool is provided by a drill collar 108. Drilling mud is pumped down the mud pipe 160 by a pump 121 returning around the tool and the entire tool is rotated by a drive 120. Coiled tubing or a drillstring may be used for coupling the drive to the downhole assembly.

The drill collar 108 provides a recess 170 for RF transmit antenna and RF receive antenna coil windings 105. Gaps in the pockets between the soft ferrite members are filled with non-conducting material 131, 135 (e.g: ceramic or high temperature plastic) and the RF coils 113, 114 are then wound over the soft ferrite members 109, 110. The soft ferrites 109, 110 and RF coil assembly 113, 114 are pressure impregnated with suitable high temperature, low viscosity epoxy resin (not shown) to harden the system against the effects of vibration, seal against drilling fluid at well pressure, and reduce the possibility of magnetoacoustic oscillations. The RF coils 113, 114 are then covered with wear plates 111 typically ceramic or other durable non-conducting material to protect them from the rock chippings flowing upwards past the tool in the borehole mud.

Because of the opposed magnet configuration, the device of Slade has an axisymmetric magnetic field and region of investigation 112 that is unaffected by tool rotation. Use of the ferrite results in a region of investigation that is close to the borehole. This is not a major problem on a MWD tool because there is little invasion of the formation by borehole drilling fluids prior to the logging. The region of investigation is within a shell with a radial thickness of about 20 mm and an axial length of about 50 mm. The gradient within the region of investigation is less than 2.7 G/cm. It is to be noted that these values are for the Slade device and, as noted above, the method of the present disclosure may also be used with other suitable NMR devices.

The method of the present disclosure is based on a representation of the acquired echo train of the earth formation by several functional parameters. In one embodiment of the disclosure, these functions are Gaussian representations of the $T_2$ distribution, but this is not to be construed as a limitation of the disclosure, and other functional distributions may be used. These Gaussian distributions represent the expected different types of fluid in the formation. In a typical reservoir we can determine clay-bound water, capillary-bound water, movable water, and hydrocarbon as separate components. Each of the Gaussians is described by its amplitude, its width, and its mean. The functional parameters can be determined by different approaches. In one embodiment of the disclosure, a chemometric-based method such as a Partial Least Squares (PLS) method is used. This allows straightforward evaluation of the echo train into several parameters.

The principles of PLS are discussed, for example, in U.S. Pat. No. 5,121,337 to Brown, the contents of which are incorporated herein by reference. The operations in PLS basically involve matrix multiplication and do not require inversion. The evaluation based on PLS models requires less memory space and execution time compared to the inversion and peak-fitting methods and can be easily implemented in a downhole system.

Figure 3B:
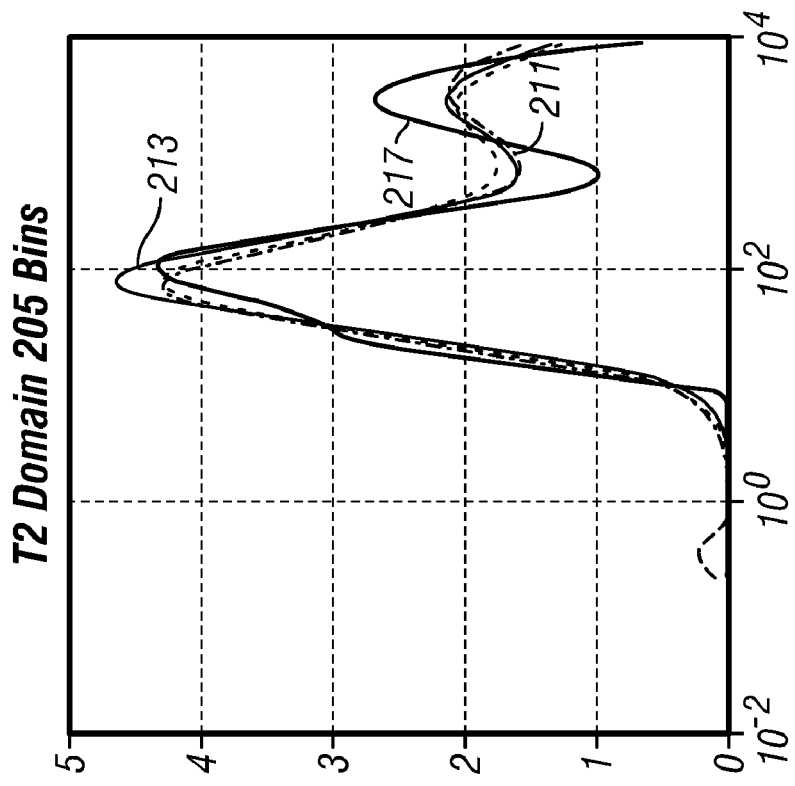
FIGS. 3A and 3B show exemplary signals and reconstructed signals in the time domain and the $T_2$ domain respectively.
Figure 3A:
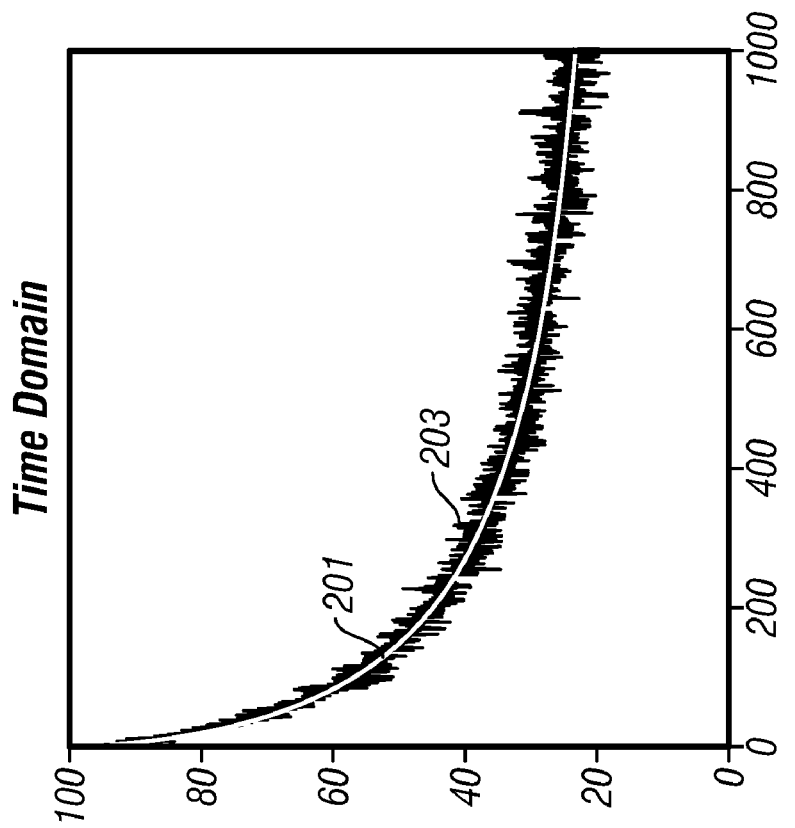

Turning now to FIGS. 3A and 3B, an example of the use of the method is given. The curve 211 is a $T_2$ distribution that was used to generate a synthetic NMR spin-echo train denoted by 201 in FIG. 3A. Noise was added to the synthetic echo train to give the time domain data denoted by 203. The curve 213 is the result of inverting the NMR echo train 203 using conventional inversion techniques. The curve 217 is a $T_2$ distribution obtained using the PLS method. The $T_2$ distribution in this case was modeled using 205 bins with the $T_2$ distribution by a plurality of Gaussian distributions. The parameters being fit are the mean, standard deviation and the amplitudes of the Gaussian distributions. In the examples shown, 3-5 Gaussian distributions were used.

Also shown in FIG. 3A but not visible due to the curve 203 are three additional curves. These additional curves are (i) a predicted echo train produced by the inverted $T_2$ distribution, and (ii) two predicted curves corresponding to the best fit Gaussian methods.

Figures 4A, 4B:
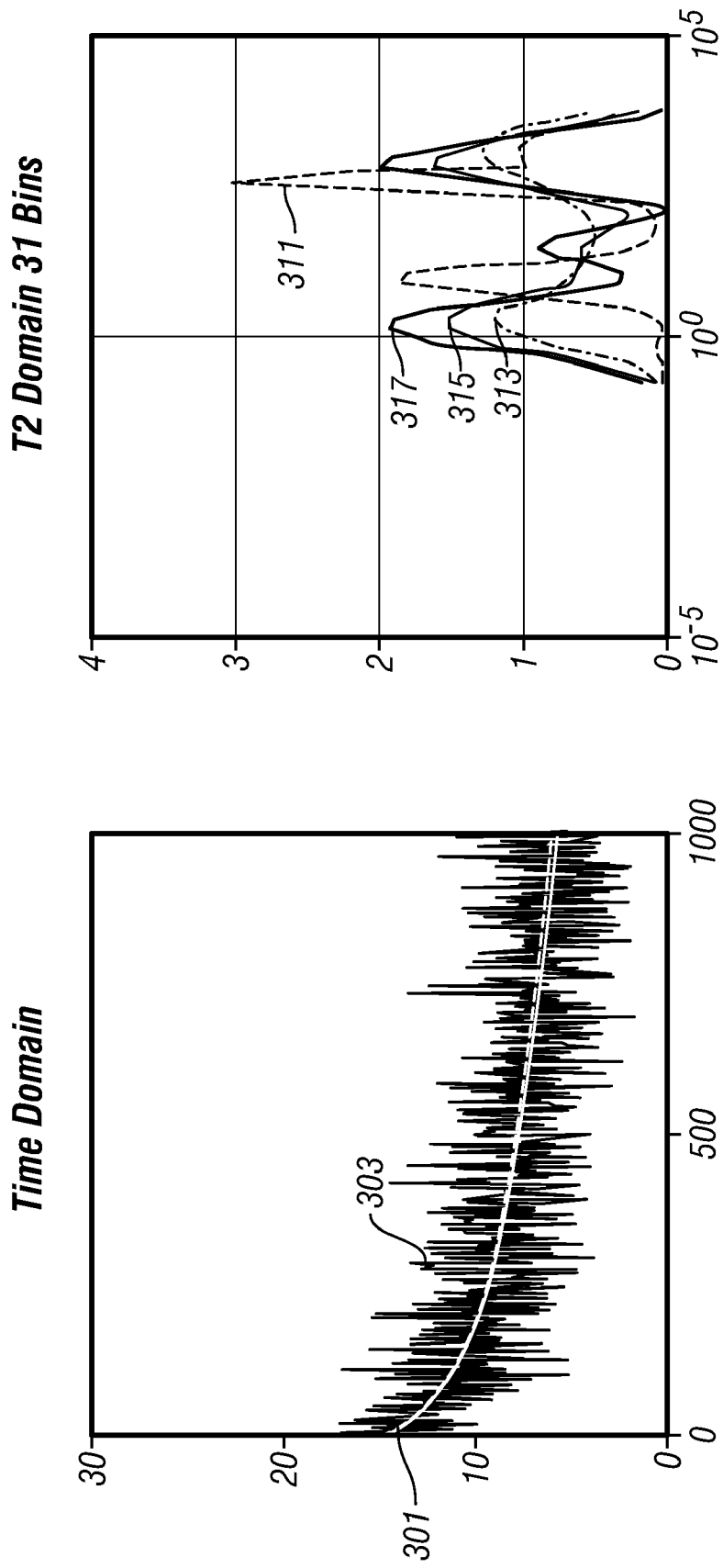
FIGS. 4A and 4B shows additional exemplary signals and reconstructed signals in the time domain and the $T_2$ domain respectively.

Turning now to FIGS. 4A and 4B, similar modeling results are shown with a higher noise level and fewer bins (31) used in the $T_2$ domain. The curve 311 is the original $T_2$ distribution, corresponding to a noise-free synthetic echo train 301. The curve 303 is a noisy version of the echo train 301. The curve 313 is the result of inverting the noisy echo train 303 using a prior art inversion method. The curve 315 is the result of the PLS method in which the mean, standard deviation and the amplitudes of the Gaussian distributions were free parameters. The curve 317 is the result of the PLS method in which the standard deviation and the amplitudes of the Gaussian distributions were free parameters. Time domain echo trains corresponding to 313, 315 and 317 are also shown in FIG. 4A but are hard to distinguish.

By the use of the Gaussian curve fitting, no more than 15 parameters have to be transmitted uphole (a maximum of three parameters for each of up to five Gaussian fits). This is a significant improvement over the transmission of one second of NMR data. At the surface, the estimated relaxation spectrum may be analyzed. For example, from the $T_2$ relaxation spectrum, using an inversion method it is possible to estimate the pore-size distribution. The use of a pore-scale geometric model used in inverting NMR spectra is described, for example, in U.S. patent application Ser. No. 11/445,023 of Georgi et al., having the same assignee as the present disclosure and the contents of which are incorporated herein by reference. The Gaussians can be used to reconstruct both the original echo train (without noise) and the corresponding representation in $T_2$ domain which then can be used to derive all further properties of interest as it is typically done in the oilfield industry.

Figure 5:
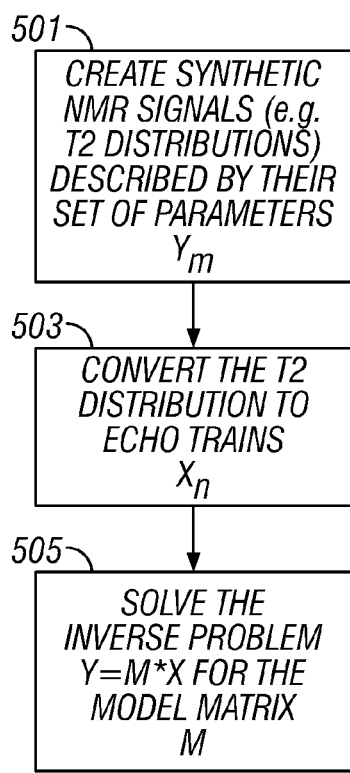
FIG. 5 is a flow chart showing further details of the implementation of the disclosure.
Figure 5:
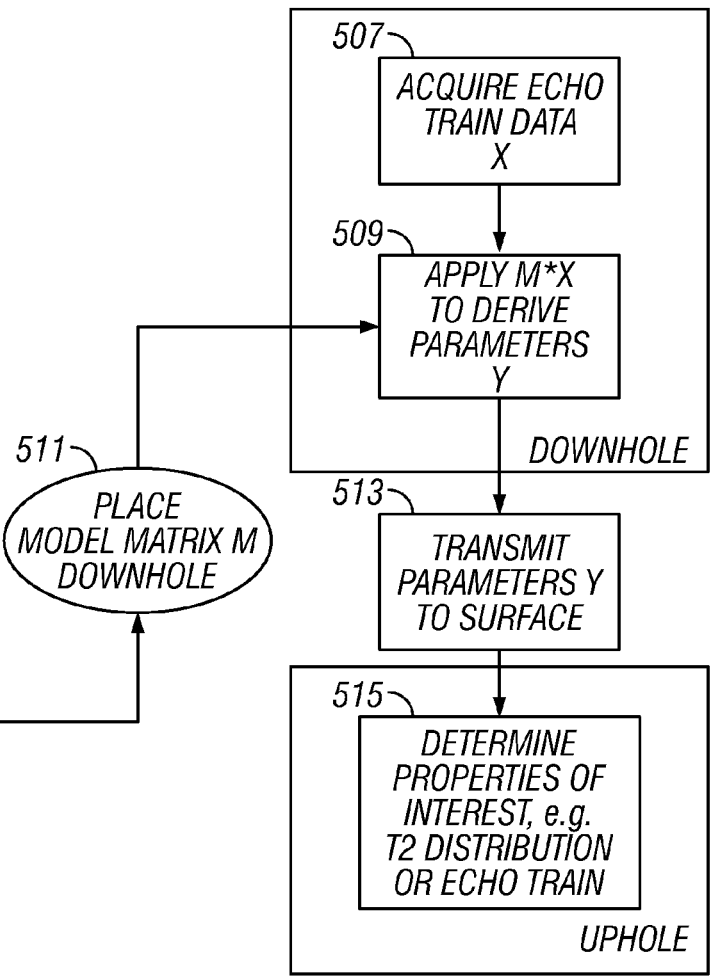

Turning now to FIG. 5, a flow chart summarizing the implementation of the method, including further details of the fitting method described above is shown. The first phase 501 of building the model involves creating synthetic NMR signals, e.g., $T_2$ distributions, described by their set of parameters $Y_m$ The $T_2$ distributions are converted 503 using known methods to echo trains $X_n$. It should be noted that the number of samples in the echo train n should be greater than or equal to the number m of parameters characterizing the $T_2$ distribution. This may be denoted by the equation:

$$Y=MX \qquad (1).$$

Eqn. (1) is inverted (discussed above and below) to give $\hat{M}$, the estimated inverse of M. The steps upto and including the determination of the inverse matrix $\hat{M}$ may be done at a surface location. The determined inverse matrix is stored on a memory of a processor in the BHA 511 and conveyed downhole.

NMR data are acquired downhole 507. Applying 509 the inverse matrix $\hat{M}$ to the acquired echo train X gives an estimate of parameters Y that characterize the acquired echo train. Steps 507, 509 are carried out downhole. The estimated parameters Y are transmitted to the surface 513. The number of bits required to do this transmission is considerably less than the number of bits that would be required to transmit the entire echo train X or a conventional $T_2$ distribution. This is an important consideration in mud pulse telemetry where bandwidth is a severe limitation. At the surface, the properties of interest, such as the echo train itself or a $T_2$ distribution of the echo train are reconstructed. Note that the operations performed downhole needed to compress the data involve only a simple matrix multiplication. The reconstruction of the $T_2$ distribution simply involves Gaussian functions.

As an alternative or a supplement to creating synthetic echo trains, actual measurements of echo trains may be made or laboratory on known samples whose properties are known, or NMR data from a rock catalog may be used for deriving the inverse matrix $\hat{M}$.

The parameters $Y_m$ can be multiple Gaussian distributions where each Gaussian is described by 3 parameters. See examples in FIGS. 4A and 4B. The parameters for each Gaussian distribution are:
 the mean $\mu_i$ of the $T_2$ location;
 the amplitude $A_i$ amplitude [p.u.]; and
 the standard deviation $\sigma_i$.

Instead of Gaussian distributions, other basis functions may be used with corresponding parameters.

Solving the inverse problem Y=M*X can be done by different methods such as partial least-squares (PLS), principal component regression (PCR), inverse least-squares (ILS), or ridge regression (RR). Further discussion of these methods is in the Hamdan application, the contents of which are incorporated herein by reference. For non-linear problems Neural Networks, neural net partial least-squares (NNPLS), locally weighted regression (LWR), or other methods can be used.

An important point of difference between Hamdan and the present disclosure is that in the former, the independent variable for the regression is a formation property. In the present disclosure, the independent variables for the regression are parameters that provide an efficient representation of the echo train (for telemetering), such as parameters of a $T_2$ distribution that, in a least-squares sense, replicates the echo train.

The recreation of properties of interest may cover $T_2$ distribution, volumetrics, permeability, echo trains, and other rock and fluid properties that are based on NMR data. It should further be noted that the method itself is of course not limited to downhole applications, As noted in Hamdan, bound volume irreducible, effective porosity, bound water, clay-bound water, and total porosity are among the formation properties that may be determined. As noted in Georgi, it is possible to estimate the pore size distribution. Determination of permeability is discussed in U.S. Pat. No. 6,686,736 to Schoen I et al., having the same assignee as the present disclosure and the contents of which are incorporated herein by reference.

In an alternate embodiment of the disclosure, instead of principal component regression or principal component analysis (PCA), a method referred to as independent component analysis (ICA) may be used. In PCA, the basis vectors are obtained by solving the algebraic eigenvalue problem $$R^T(XX^T)R=\Lambda$$

where X is a data matrix whose columns are training samples (with the mean values removed), R is a matrix of eigenvectors, and $\Lambda$ is the corresponding diagonal matrix of eigenvalues. With such a representation, the projection of data, $C_n=R_n^T X$, from the original p dimensional space to a subspace spanned by n principal eigenvectors is optimal in the mean squared error sense. That is, the reprojection of $C_n$ back into the p dimensional space has minimum reconstruction error. In fact, if n is large enough to include all the eigenvectors with non-zero eigenvalues, the reprojection is lossless. The goal in PCA is to minimize the reconstruction error from compressed data.

In ICA, on the other hand the goal is to minimize the statistical dependence between the basis vectors. Mathematically, this can be written as $WX^T=U$, where ICA searches for a linear transformation W that minimizes the statistical dependence between the rows of U, given a training set X (as before). Unlike PCA, the basis vectors in ICA are neither orthogonal nor ranked in order. Also, there is no closed form expression to find W. Instead iterative algorithms have to be used. See Baek et al., PCA vs. ICA: A comparison on the FERET data set.

As noted by Baek, global properties are better represented by PCA while local structure is better represented by ICA. Based on a comparison of PCA to ICA, Baek concluded that for facial recognition problems (that are holistic in nature), PCA gave superior results. Baek further conjectured that evaluations on localized recognition tasks, such as recognizing facial expressions, ICA may give better results.

First and foremost, NMR measurements are indicative of the pore-size distribution in an earth formation. Secondarily, they are indicative of fluid types. By their very nature, the primary pore-size distribution in sedimentary rocks reflects the depositional energy, something that is episodic. Hence a significant amount of local structure is to be expected in the pore-size distribution. To put it another way, one would, for example, expect a high correlation between occurrences of pore-sizes of 1 μm and 1.01 μm: this would imply a local structure in the $T_2$ distribution and the $T_1$ distribution. In addition, the presence of heavy oil in a formation would also imply a local structure in the relaxation time distributions—once heavy oil has formed, it cannot be undone to light oil.

We next discuss implementation of ICA and differences with PCA. NMR relaxation of fluids in rocks exhibits multi-exponential behavior, which can be expressed in a discrete model as follows:

$$E(t) = \sum_j A_j e^{\left(\frac{t}{T_{2j}}\right)} \tag{2}$$

Assuming $T_{2j}$=0.2 ... 8192 using increment of $2^{(1/4)}$, then $T_2$ will have a length of 64.

This will translate into matrix notation when sampling the t at TE=0.6 μs and 1000 samples as:

$$E_{1\times 1000}=A_{1\times 64}\times F_{64\times 1000} \tag{3},$$

where $A_j$ is proportional to the proton population of pores which have a relaxation time of $T_{2j}$, E(t) is the resultant echo-train in continuous time and E is discretized version of E(t). We first map all possible echo-trains with single exponential decay constant into a matrix F. Next, Through Independent Component Analysis we decompose the F matrix into 2 matrices.

$$F_{64\times 1000}=M_{64\times 64}\times S_{64\times 1000} \tag{4}$$

F is a matrix that spans all single components decays in the echo train space.

S is a matrix of independent components (latent variables) of the corresponding type of acquisition (Created from ICA (Independent component analysis), using the fastICA algorithm, available with MATLAB, of the F matrix). M is the mixing matrix. Both M and S need to be estimated. Once S and M are found the manner of compressing data is as follows:

$$E_{1\times1000} = A_{1\times64} \times M_{64\times64} \times S_{64\times1000} \quad (5)$$

let $$Comp_{1\times64} = A_{1\times64} \times M_{64\times64} \quad (5a)$$

Comp is called the Compression vector. Eqn 5. can then be written into:

$$E_{1\times1000} = Comp_{1\times64} S_{64\times1000} \quad (6)$$

Now multiply to the right both sides by inverse of $S \Rightarrow S^{-1}$.

$$E_{1\times1000} \times S^{-1}{}_{1\times64} = Comp_{1\times64} S_{64\times1000} \times S^{-1}{}_{1000\times64}$$

which leads to $$E_{1\times1000} \times S^{-1}{}_{1000\times64} = Comp_{1\times64} \quad (7)$$

But the eigenanalysis of the Covariance of F tells us that beyond component 6 there will be almost zero percent of variance left as the following table shows:

TABLE 1

Analysis of the variance contribution in each eigenvector of the Covariance(F)

| Eigenvector Number Of Cov(F) | Eigenvalue of Cov(F) | Variance of this Component [%] | Variance of previous + this Component [%] |
|---|---|---|---|
| 1 | 214.0 | 94.3923 | 94.3923 |
| 2 | 10.70 | 4.7247 | 99.1171 |
| 3 | 1.57 | 0.6920 | 99.8091 |
| 4 | 0.327 | 0.1439 | 99.9530 |
| 5 | 0.0790 | 0.0348 | 99.9878 |
| 6 | 0.0203 | 0.0090 | 99.9968 |
| 7 | 0.00537 | 0.0024 | 99.9991 |
| 8 | 0.001420 | 0.0006 | 99.9998 |
| 9 | 0.000376 | 0.0002 | 99.9999 |
| 10 | 0.0000984 | 0.0000 | 100.0000 |
| 11 | 0.00002550 | 0.0000 | 100.0000 |
| 12 | 0.00000651 | 0.0000 | 100.0000 |
| 13 | 0.00000164 | 0.0000 | 100.0000 |
| 14 | 0.00000041 | 0.0000 | 100.0000 |
| 15 | 0.00000010 | 0.0000 | 100.0000 |

Thus Eqn. 7 can be reduced into:

$$E_{1\times1000} \times S^{-1}{}_{1000\times6} = Comp_{1\times6} \quad (8)$$

Eqn. 8 is applied in the downhole tool for compression of echo trains.

Eqn. 6 becomes Eqn. 9 and is applied in the surface system to decompress the mud-pulse-transmitted data:

$$E_{1\times1000} = Comp_{1\times6} \times S_{6\times1000} \quad (9)$$

Eqn. 8 tells us that providing the inverse of a reduced form of the S matrix, we can compress an echo-train of length 1000, (and if we have an echo-train of length N, we need to create the S matrix of size 6×N), into a 1×6 matrix. Furthermore Eqn. 9 tells us we could recover the echo-train by using the same model (independent components) and the corresponding compression.

The PCA algorithm differ from the ICA only in the way of decomposition Through Principal Component Analysis we decompose the F matrix into 2 matrices.

$$F_{64\times1000} = Scores_{64\times64} \times Loads_{64\times1000} \quad (10),$$

Where F is a matrix that spans all single components decays, Loads is a matrix of eigenvectors of the corresponding type of acquisition (Created from Principal components decomposition of the F matrix) and scores are the eigenvalues of Matrix F. It is to be noted that Scores forms an orthogonal set ($Scores_i^T Scores_j = 0$ for $i \neq j$) and Loads forms an orthonormal set ($Loads_i^T Loads_j = 0$ for $i \neq j$ and $=1$ for $i=j$) $\Rightarrow Loads^T = Loads^{-1}$. The scores $Scores_i$ of T is a linear combination of F defined by $Loads_i$ that is to say that $Scores_i$ is the projection of F on $Loads_i$. by replacing the value of F in Eqn. 10 into Eqn. 3

$$E_{1\times1000} = A_{1\times64} \times Scores_{64\times64} \times Loads_{64\times1000} \quad (11).$$

Let $$Comp_{1\times64} = A_{1\times64} \times Scores_{64\times64} \quad (11a)$$

Comp is what we call a Compression vector. Eqn. 11a can then be written into:

$$E_{1\times1000} = Comp_{1\times64} \times Loads_{64\times1000} \quad (12)$$

Now multiplying to the right by inverse of $Loads \Rightarrow Loads^{-1}$, and using the fact that $Loads^{-1} = Loads^T$ $$E_{1\times1000} \times Loads^T{}_{1000\times64} = Comp_{1\times64} \times Loads_{64\times1000} \times Loads^T{}_{1000\times64}$$

which leads to $$E_{1\times1000} \times Loads^T{}_{1000\times64} = Comp_{1\times64} \quad (13)$$

Eqn. 13 tells us that we could compress the whole Echo-Train from 1000 points into 64 points without losing any information. Analysis of PCA tells us that beyond component 5 there will be almost zero percent of variance left as the following table shows:

TABLE 2

Analysis of the variance contribution in each PCA component

| Principal Component | Eigenvalue of Cov(F) | Variance of this Component [%] | Variance of previous + this Component [%] |
|---|---|---|---|
| 1 | 214.0 | 94.3923 | 94.3923 |
| 2 | 10.70 | 4.7247 | 99.1171 |
| 3 | 1.57 | 0.6920 | 99.8091 |
| 4 | 0.327 | 0.1439 | 99.9530 |
| 5 | 0.0790 | 0.0348 | 99.9878 |
| 6 | 0.0203 | 0.0090 | 99.9968 |
| 7 | 0.00537 | 0.0024 | 99.9991 |
| 8 | 0.001420 | 0.0006 | 99.9998 |
| 9 | 0.000376 | 0.0002 | 99.9999 |
| 10 | 0.0000984 | 0.0000 | 100.0000 |
| 11 | 0.00002550 | 0.0000 | 100.0000 |
| 12 | 0.00000651 | 0.0000 | 100.0000 |
| 13 | 0.00000164 | 0.0000 | 100.0000 |
| 14 | 0.00000041 | 0.0000 | 100.0000 |
| 15 | 0.00000010 | 0.0000 | 100.0000 |

Thus Eqn. 13 can be reduced into:

$$E_{1\times1000} \times Loads^T{}_{1000\times5} = Comp_{1\times5} \quad (14)$$

and Eqn. 12 becomes:

$$E_{1\times1000} = Comp_{1\times5} \times Loads_{5\times1000} \quad (15)$$

Eqn. 14 tells us that providing a reduced form of the Loads matrix, we can compress an Echo-Train of length 1000, (and if we have an Echo-train of length N, we need to create the Loads matrix of size 5×N), into 1×5 matrix. Furthermore Eqn. 15 tells us we could recover the echo-train by using the same model and the corresponding compression.

To summarize, the ICA algorithm can be basically be used as a replacement of the PCA.

Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

What is claimed is:

1. A method of determining a property of an earth formation, the method comprising:
   conveying a nuclear magnetic resonance (NMR) sensing apparatus into a borehole;
   using the NMR sensing apparatus for obtaining a signal indicative of the property of the earth formation;
   using only a multiplication of the signal by a predetermined matrix for providing a parametric representation of a distribution of a relaxation time of nuclear spins in terms of at least one predefined basis function at a downhole location, the parametric representation requiring fewer bits for transmission than the signal;
   telemetering the parametric representation to a surface location; and
   at the surface location, using the telemetered parametric representation to estimate value of the property of the earth formation.

2. The method of claim 1 wherein:
   (i) the signal comprises a spin echo signal, and
   (ii) the representation of relaxation of nuclear spins comprises a transverse relaxation time ($T_2$) distribution.

3. The method of claim 1 wherein:
   (i) the at least one basis function comprises a Gaussian function, and
   (ii) the parametric representation includes a mean, a standard deviation, and an amplitude of the Gaussian function.

4. The method of claim 1 further comprising defining the predetermined matrix by performing a regression analysis on at least one of: (i) synthetic NMR signals, and (ii) NMR signals measured on samples having known properties.

5. The method of claim 4 wherein a dependent variable in the regression analysis comprises a spin echo signal.

6. The method of claim 4 wherein the regression analysis is selected from the group consisting of: (A) partial least-squares, (B) principal component regression, (C) inverse least-squares, (D) ridge regression, (E) Neural Networks, (F) neural net partial least-squares, and (G) locally weighted regression.

7. The method of claim 1 wherein the determined property is at least one of: (i) bound volume irreducible, (ii) effective porosity, (iii) bound water, (iv) clay-bound water, (v) total porosity, (vi) a permeability, and (vii) a pore size distribution.

8. The method of claim 1 further comprising conveying the NMR sensing apparatus into the borehole on a bottomhole assembly using a drilling tubular.

9. An apparatus for determining a property of an earth formation, the apparatus comprising:
   a nuclear magnetic resonance (NMR) sensing apparatus configured to be conveyed into a borehole and obtain a signal indicative of the property of the earth formation;
   a downhole processor configured to:
   (i) use only a multiplication of the signal by a predetermined matrix to provide a parametric representation of a distribution of a relaxation time of nuclear spins in terms of at least one predefined basis function, and
   (ii) telemeter the parametric representation to a surface location; and
   a surface processor configured to use the telemetered parametric representation to estimate a value of the property of the earth formation.

10. The apparatus of claim 9 wherein:
    (i) the signal that the NMR sensing apparatus is configured to produce obtain further comprises a spin echo signal, and
    (ii) the representation of relaxation of nuclear spins further comprises transverse relaxation time $T_2$ distribution.

11. The apparatus of claim 9 wherein:
    (i) the at least one basis function the downhole processor is configured to use comprises a Gaussian function, and
    (ii) the parametric representation the downhole processor is configured to provide includes a mean, a standard deviation, and an amplitude of the Gaussian function.

12. The apparatus of claim 9 wherein the predetermined matrix is defined by a processor configured to perform a regression analysis on at least one of: (i) synthetic NMR signals, and (ii) NMR signals measured on samples having known properties.

13. The apparatus of claim 12 wherein a dependent variable in the regression analysis comprises a spin echo signal.

14. The apparatus of claim 12 wherein the regression analysis the processor is configured to perform is selected from the group consisting of: (A) partial least-squares, (B) principal component regression, (C) inverse least-squares, (D) ridge regression, (E) Neural Networks, (F) neural net partial least-squares, and (G) locally weighted regression.

15. The apparatus of claim 9 wherein the property the surface processor is configured to determine is at least one of: (i) bound volume irreducible, (ii) effective porosity, (iii) bound water, (iv) clay-bound water, (v) total porosity, (vi) a permeability, and (vii) a pore size distribution.

16. The apparatus of claim 9 further comprising a drilling tubular configured to convey a bottomhole assembly including the NMR sensing device into the borehole.

17. At least one non-transitory computer readable medium having instructions stored thereon instructions which when read by at least one processor cause the at least one processor to execute a method, the method comprising:
    using only a multiplication by a predetermined matrix to estimate from of a signal obtained by a nuclear magnetic resonance (NMR) sensing apparatus in a borehole for providing a parametric representation of relaxation of a distribution of a relaxation time of nuclear spins in terms of at least one predefined basis function, the parametric representation requiring fewer bits for transmission than the signal;
    telemetering the parametric representation to a surface location; and
    using the telemetered parametric representation to estimate for estimating a value of a property of the earth formation.

18. The at least one medium of claim 17 wherein the medium is selected from the group consisting of (i) a ROM, (ii) an EPROM, (iii) an EEPROM, (iv) a flash memory, and (v) an optical disk.

* * * * *